United States Patent
Weidman (10) Patent No.: US 10,390,925 B2
(45) Date of Patent: *Aug. 27, 2019

(54) MIGRATION RESISTANT EMBOLIC FILTER

(71) Applicant: C.R. Bard, Inc., Murray Hill, NJ (US)

(72) Inventor: Jenna Weidman, Tempe, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,442

(22) Filed: Jun. 27, 2014

(65) Prior Publication Data

US 2014/0343597 A1 Nov. 20, 2014

Related U.S. Application Data (63) Continuation of application No. 11/735,185, filed on Apr. 13, 2007, now Pat. No. 8,795,351.

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01); *A61F 2230/005* (2013.01); *A61F 2230/008* (2013.01); *A61F 2230/0067* (2013.01)

(58) Field of Classification Search
CPC ...... A61F 2/013; A61F 2/01; A61F 2002/011; A61F 2230/00; A61F 2/20; A61B 17/12022; A61B 2017/1205
See application file for complete search history.

(56) References Cited

U.S. PATENT DOCUMENTS

| | | |
|---|---|---|
| 3,540,431 A | 11/1970 | Mobin-Uddin |
| 3,952,747 A | 4/1976 | Kimmell, Jr. |
| 4,425,908 A | 1/1984 | Simon |
| 4,494,531 A | 1/1985 | Gianturco |
| 4,619,246 A | 10/1986 | Molgaard-Nielsen et al. |
| 4,643,184 A | 2/1987 | Mobin-Uddin |
| 4,727,873 A | 3/1988 | Mobbin-Uddin |
| 4,793,348 A | 12/1988 | Palmaz |
| 4,817,600 A | 4/1989 | Herms et al. |
| 4,990,156 A | 2/1991 | Lefebvre |
| 5,059,205 A | 10/1991 | Ei-Nounou et al. |

(Continued)

FOREIGN PATENT DOCUMENTS

WO 2005102211 11/2005

OTHER PUBLICATIONS

PCT/US2008/059906 International Search Report dated Aug. 29, 2008.

(Continued)

*Primary Examiner* — Kathleen S Holwerda
*Assistant Examiner* — Christina C Lauer
(74) *Attorney, Agent, or Firm* — Garvey, Smith & Nehrbass, Patent Attorneys, L.L.C.; Charles C. Garvey, Jr.; Seth M. Nehrbass (57) ABSTRACT

An embolic filter is disclosed and can include a head. A plurality of bent legs can extend from the head. Each bent leg can be configured to engage an inner wall of a vein and prevent the embolic filter from migrating in a cranial direction. A plurality of straight legs can also extend from the head. Each straight leg can be configured to prevent the embolic filter from migrating in a caudal direction.

26 Claims, 10 Drawing Sheets

(56) References Cited

U.S. PATENT DOCUMENTS

| | | | |
|---|---|---|---|
| 5,108,418 A | 4/1992 | Lefebvre | |
| 5,133,733 A | 7/1992 | Rasmussen et al. | |
| 5,234,458 A | 8/1993 | Metais | |
| 5,242,462 A | 9/1993 | Ei-Nounou et al. | |
| 5,300,086 A | 4/1994 | Gorry et al. | |
| 5,324,304 A | 6/1994 | Rasmussen | |
| 5,344,427 A | 9/1994 | Cottenceau et al. | |
| 5,350,398 A | 9/1994 | Pavcnik et al. | |
| 5,370,657 A | 12/1994 | Irie | |
| 5,383,887 A | 1/1995 | Nadal | |
| 5,601,595 A | 2/1997 | Smith | |
| 5,626,605 A | 5/1997 | Irie et al. | |
| 5,634,942 A | 6/1997 | Chevillon et al. | |
| 5,669,933 A * | 9/1997 | Simon | A61F 2/01 600/191 |
| 5,681,347 A | 10/1997 | Cathcart et al. | |
| 5,683,411 A | 11/1997 | Kavteladze et al. | |
| 5,709,704 A | 1/1998 | Nott et al. | |
| 5,725,550 A | 3/1998 | Nadal | |
| 5,746,767 A | 5/1998 | Smith | |
| 5,800,457 A | 9/1998 | Gelbfish | |
| 5,836,968 A | 11/1998 | Simon et al. | |
| 5,836,969 A | 11/1998 | Kim et al. | |
| 5,853,420 A | 12/1998 | Chevillon et al. | |
| 5,911,733 A | 6/1999 | Parodi | |
| 5,941,896 A | 8/1999 | Kerr | |
| 5,968,071 A | 10/1999 | Chevillon et al. | |
| 5,984,947 A | 11/1999 | Smith | |
| 6,007,558 A * | 12/1999 | Ravenscroft | A61F 2/01 606/194 |
| 6,013,093 A | 1/2000 | Nott et al. | |
| 6,080,178 A | 6/2000 | Meglin | |
| 6,126,673 A | 10/2000 | Kim et al. | |
| 6,146,404 A | 11/2000 | Kim et al. | |
| 6,152,946 A | 11/2000 | Broome et al. | |
| 6,165,179 A | 12/2000 | Cathcart et al. | |
| 6,171,327 B1 | 1/2001 | Daniel et al. | |
| 6,193,739 B1 | 2/2001 | Chevillon et al. | |
| 6,214,025 B1 | 4/2001 | Thistle et al. | |
| 6,231,589 B1 | 5/2001 | Wessman et al. | |
| 6,251,122 B1 | 6/2001 | Tsukernik | |
| 6,267,776 B1 | 7/2001 | O'Connell | |
| 6,273,901 B1 | 8/2001 | Whitcher et al. | |
| 6,331,183 B1 | 12/2001 | Suon | |
| 6,342,062 B1 | 1/2002 | Suon et al. | |
| 6,342,063 B1 | 1/2002 | DeVries et al. | |
| 6,383,193 B1 | 5/2002 | Cathcart et al. | |
| 6,391,045 B1 | 5/2002 | Kim et al. | |
| 6,416,530 B2 | 7/2002 | DeVries et al. | |
| 6,436,120 B1 | 8/2002 | Meglin | |
| 6,443,972 B1 | 9/2002 | Bosma et al. | |
| 6,447,530 B1 | 9/2002 | Ostrovsky et al. | |
| 6,468,290 B1 | 10/2002 | Weldon et al. | |
| 6,506,205 B2 | 1/2003 | Goldberg et al. | |
| 6,517,559 B1 | 2/2003 | O'Connell | |
| 6,540,767 B1 | 4/2003 | Walak et al. | |
| 6,551,342 B1 | 4/2003 | Shen et al. | |
| 6,558,404 B2 | 5/2003 | Tsukernik | |
| 6,569,183 B1 | 5/2003 | Kim et al. | |
| 6,575,997 B1 | 6/2003 | Palmer et al. | |
| 6,582,447 B1 | 6/2003 | Patel et al. | |
| 6,589,266 B2 | 7/2003 | Whitcher et al. | |
| 6,592,607 B1 | 7/2003 | Palmer et al. | |
| 6,641,590 B1 | 11/2003 | Palmer et al. | |
| 6,652,558 B2 | 11/2003 | Patel et al. | |
| 6,706,054 B2 | 3/2004 | Wessman et al. | |
| 6,716,208 B2 | 4/2004 | Humes | |
| 6,872,217 B2 | 3/2005 | Walak et al. | |
| 6,881,218 B2 | 4/2005 | Beyer et al. | |
| 6,932,832 B2 | 8/2005 | Patel et al. | |
| 6,972,025 B2 * | 12/2005 | WasDyke | A61F 2/01 606/200 |
| 6,994,092 B2 | 2/2006 | van der Burg et al. | |
| 7,001,424 B2 | 2/2006 | Patel et al. | |
| 7,004,955 B2 | 2/2006 | Shen et al. | |
| 7,004,956 B2 | 2/2006 | Palmer et al. | |
| 7,033,376 B2 | 4/2006 | Tsukernik | |
| 7,041,117 B2 | 5/2006 | Suon et al. | |
| 7,147,649 B2 | 12/2006 | Thomas | |
| 2001/0000799 A1 | 5/2001 | Wessman et al. | |
| 2001/0011181 A1 | 8/2001 | DiMatteo | |
| 2001/0023358 A1 | 9/2001 | Tsukernik | |
| 2001/0025187 A1 | 9/2001 | Okada | |
| 2001/0039431 A1 | 11/2001 | DeVries | |
| 2001/0039432 A1 | 11/2001 | Whitcher et al. | |
| 2002/0045918 A1 | 4/2002 | Suon et al. | |
| 2002/0116024 A1 | 8/2002 | Goldberg et al. | |
| 2002/0138097 A1 | 9/2002 | Ostrovsky et al. | |
| 2002/0193828 A1 | 12/2002 | Griffin et al. | |
| 2003/0040772 A1 | 2/2003 | Hyodoh et al. | |
| 2003/0097145 A1 | 5/2003 | Goldberg et al. | |
| 2003/0109897 A1 | 6/2003 | Walak et al. | |
| 2003/0139765 A1 | 7/2003 | Patel et al. | |
| 2003/0153945 A1 | 8/2003 | Patel et al. | |
| 2003/0163159 A1 | 8/2003 | Patel et al. | |
| 2003/0176888 A1 | 9/2003 | O'Connell | |
| 2003/0199918 A1 | 10/2003 | Patel et al. | |
| 2003/0208227 A1 | 11/2003 | Thomas | |
| 2003/0208253 A1 | 11/2003 | Beyer et al. | |
| 2004/0006369 A1 | 1/2004 | DiMatteo | |
| 2004/0059373 A1 | 3/2004 | Shapiro et al. | |
| 2004/0073252 A1 | 4/2004 | Goldberg et al. | |
| 2004/0093017 A1 | 5/2004 | Chanduszko | |
| 2004/0158273 A1 | 8/2004 | Weaver et al. | |
| 2004/0158274 A1 | 8/2004 | WasDyke | |
| 2004/0186510 A1 | 9/2004 | Weaver | |
| 2004/0230220 A1 | 11/2004 | Osborne | |
| 2005/0027314 A1 | 2/2005 | WasDyke | |
| 2005/0055045 A1 | 3/2005 | DeVries et al. | |
| 2005/0107822 A1 | 5/2005 | WasDyke | |
| 2005/0131452 A1 | 6/2005 | Walak et al. | |
| 2005/0159771 A1 | 7/2005 | Petersen | |
| 2005/0165441 A1 | 7/2005 | McGuckin et al. | |
| 2005/0165442 A1 | 7/2005 | Thinnes et al. | |
| 2005/0182439 A1 | 8/2005 | Lowe | |
| 2005/0203566 A1 | 9/2005 | Beulke | |
| 2005/0209632 A1 | 9/2005 | Wallace | |
| 2005/0234503 A1 * | 10/2005 | Ravenscroft | A61F 2/01 606/200 |
| 2005/0234504 A1 | 10/2005 | WasDyke | |
| 2005/0251197 A1 | 11/2005 | Hensley et al. | |
| 2005/0251199 A1 | 11/2005 | Osborne et al. | |
| 2005/0267512 A1 | 12/2005 | Osborne et al. | |
| 2005/0267513 A1 | 12/2005 | Osborne et al. | |
| 2005/0267514 A1 | 12/2005 | Osborne et al. | |
| 2005/0267515 A1 | 12/2005 | Olivia et al. | |
| 2005/0277977 A1 | 12/2005 | Thornton | |
| 2005/0288703 A1 | 12/2005 | Beyer et al. | |
| 2005/0288704 A1 | 12/2005 | Cartier et al. | |
| 2006/0004402 A1 | 1/2006 | Voeller et al. | |
| 2006/0015137 A1 | 1/2006 | WasDyke et al. | |
| 2006/0030875 A1 | 2/2006 | Tessmer | |
| 2006/0036279 A1 | 2/2006 | Eidenschink et al. | |
| 2006/0069405 A1 | 3/2006 | Schaeffer et al. | |
| 2006/0069406 A1 | 3/2006 | Hendriksen et al. | |
| 2006/0079928 A1 | 4/2006 | Cartier et al. | |
| 2006/0079930 A1 * | 4/2006 | McGuckin, Jr. | A61F 2/01 606/200 |
| 2006/0095068 A1 | 5/2006 | WasDyke et al. | |
| 2006/0100660 A1 | 5/2006 | Osborne et al. | |
| 2006/0106417 A1 | 5/2006 | Tessmer et al. | |
| 2006/0178695 A1 | 8/2006 | Decant et al. | |
| 2006/0184193 A1 | 8/2006 | Lowe et al. | |
| 2006/0206138 A1 | 9/2006 | Eidenschink | |
| 2006/0259067 A1 | 11/2006 | Welch et al. | |

(56) References Cited

U.S. PATENT DOCUMENTS

2007/0005095 A1 1/2007 Osborne et al.
2007/0032816 A1 2/2007 O'Connell et al.

OTHER PUBLICATIONS

PCT/US2008/059906 International Preliminary Report on Patentability dated Oct. 13, 2009.

* cited by examiner

MIGRATION RESISTANT EMBOLIC FILTER

FIELD OF THE DISCLOSURE

The present disclosure relates generally to surgical devices. More specifically, the present disclosure relates to embolic filters.

BACKGROUND

A pulmonary embolism (PE) is a blockage of the pulmonary artery, or a branch of the pulmonary artery, by a blood clot, fat, air, a clump of tumor cells, or other embolus. The most common form of pulmonary embolism is a thromboembolism. A thromboembolism can occur when a venous thrombus, i.e., a blood clot, forms in a patient, becomes dislodged from the formation site, travels to the pulmonary artery, and becomes embolized in the pulmonary artery. When the blood clot becomes embolized within the pulmonary artery and blocks the arterial blood supply to one of the patient's lungs, the patient can suffer symptoms that include difficult breathing, pain during breathing, and circulatory instability. Further, the pulmonary embolism can result in death of the patient.

Commons sources of embolism are proximal leg deep venous thrombosis (DVTs) and pelvic vein thromboses. Any risk factor for DVT can also increase the risk that the venous clot will dislodge and migrate to the lung circulation. One major cause of the development of thrombosis includes alterations in blood flow. Alterations in blood flow can be due to immobilization after surgery, immobilization after injury, and immobilization due to long-distance air travel. Alterations in blood flow can also be due to pregnancy and obesity.

A common treatment to prevent pulmonary embolism includes anticoagulant therapy. For example, heparin, low molecular weight heparins (e.g., enoxaparin and dalteparin), or fondaparinux can be administered initially, while warfarin therapy is commenced. Typically, warfarin therapy can last three to six months. However, if a patient has experienced previous DVTs or PEs, warfarin therapy can last for the remaining life of the patient.

If anticoagulant therapy is contraindicated, ineffective, or both, an embolic filter can be implanted within the inferior vena cava of the patient. An embolic filter, i.e., an inferior vena cava filter, is a vascular filter that can be implanted within the inferior vena cava of a patient to prevent PEs from occurring within the patient. The embolic filter can trap embolus and prevent the embolus from travelling the pulmonary artery.

An embolic filter can be permanent or temporary. Further, an embolic filter can be placed endovascularly, i.e., the embolic filter can be inserted into the inferior vena cava via the blood vessels of the patient. Modern filters have the capability to be compressed into relatively thin diameter catheters. Further, modern filters can be placed via the femoral vein, the jugular vein, or via the arm veins. The choice of route for installing the embolic filter can depend on the amount of blood clot, the location of the blot clot within the venous system, or a combination thereof.

The blood clot can be located using magnetic resonance imaging (MRI). Further, the filter can be placed using a filter delivery system that includes a catheter. The catheter can be guided into the IVC using fluoroscopy. Then, the filter can be pushed from the catheter and deployed into the desired location within the IVC. Typically, a filter can be anchored to prevent migration through the IVC.

Accordingly, there is a need for an improved embolic filter that has desired functionality and stability.

DETAILED DESCRIPTION OF THE DRAWINGS

An embolic filter is disclosed and can include a head. A plurality of bent legs can extend from the head. Each bent leg can be configured to engage an inner wall of a vein and prevent the embolic filter from migrating in a cranial direction. A plurality of straight legs can also extend from the head. Each straight leg can be configured to prevent the embolic filter from migrating in a caudal direction.

In another embodiment, an embolic filter is disclosed and can include a head. A first plurality of legs can extend from the head. Each of the first plurality of legs can be configured to engage an inner wall of a vein and prevent the embolic filter from migrating in a cranial direction. Also, each of the first plurality of legs can include a first leg diameter. The embolic filter can also include a second plurality of legs that can extend from the head. Each of the second plurality of legs can be configured to prevent the embolic filter from migrating in a caudal direction and each of the second plurality of legs can have a second leg diameter that is at least 1.2 times greater than the first leg diameter.

In yet another embodiment, an embolic filter is disclosed and can include a head. A first bent arm, a second bent arm, a third bent arm, a fourth bent arm, a fifth bent arm, and a sixth bent arm can extend from the head. Each bent arm can include a proximal end and a bent arm diameter. Moreover, a first bent leg, a second bent leg, and a third bent leg can extend from the head. Each bent leg can include a proximal end and a bent leg diameter that is substantially equal to the bent arm diameter. In this embodiment, a first straight leg, a second straight leg, and a third straight leg can extend from the head. Each straight leg has a proximal end and a straight leg diameter that is at least 1.2 times greater than the bent leg diameter or the bent arm diameter.

Description of the Relevant Anatomy

Figure 1:
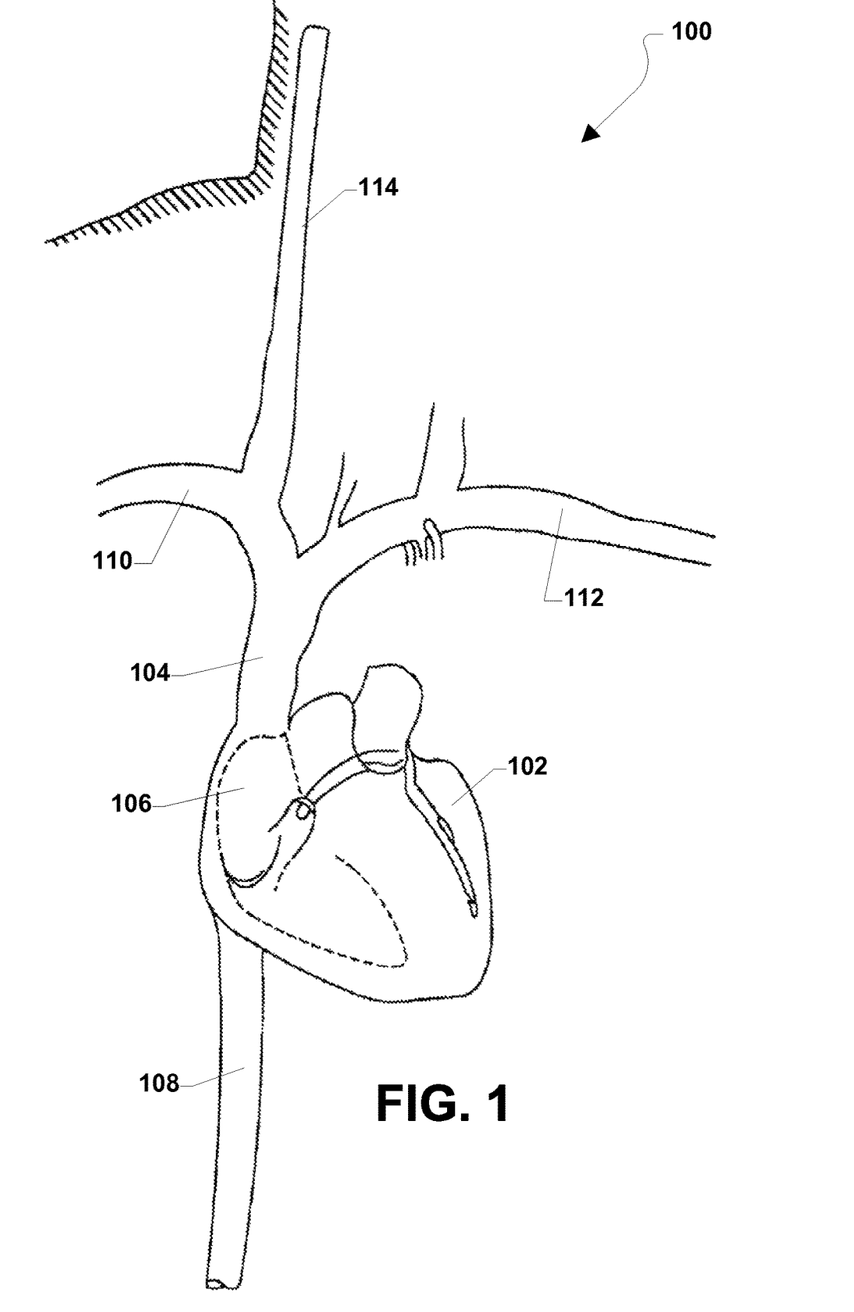
FIG. 1 is a diagram of a portion of a cardiovascular system.

Referring to FIG. 1, a portion of a cardiovascular system is shown and is generally designated 100. As shown, the system can include a heart 102. A superior vena cava 104 can communicate with the heart 102. Specifically, the superior vena cava 104 can provide blood flow into a right atrium 106 of the heart 102 from the generally upper portion of a human body. As shown, an inferior vena cava 108 can also communicate with the heart. The inferior vena cava 108 can also provide blood flow into the right atrium 106 of the heart 102 from the lower portion of the cardiovascular system. FIG. 1 also shows a right subclavian vein 110, a left subclavian vein 112, and a jugular vein 114 that can communicate with the superior vena cava 104.

Description of a Filter Delivery Device

Figure 2:
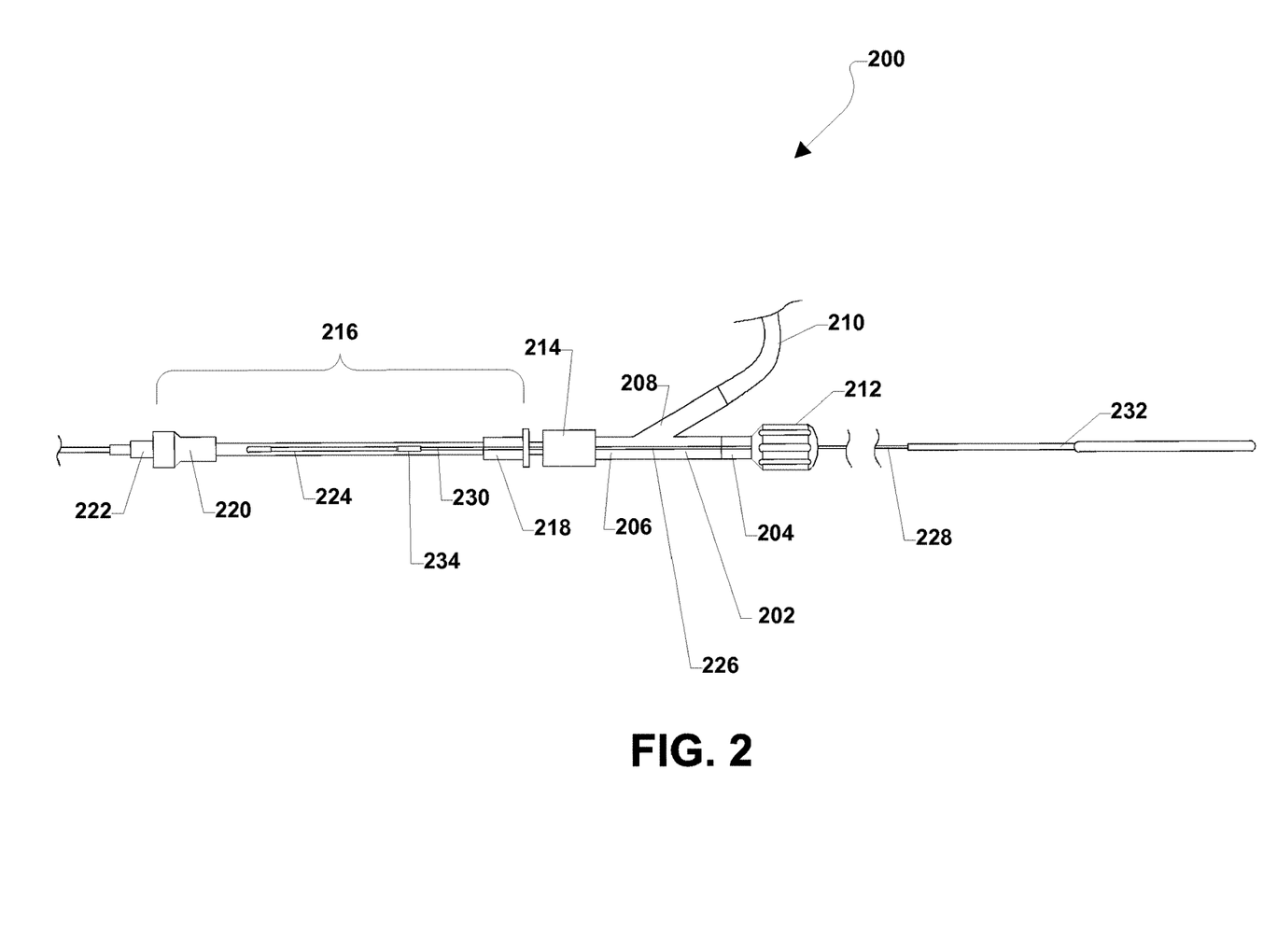
FIG. 2 is a plan view of a filter delivery device.

FIG. 2 illustrates a filter delivery device, designated 200. As shown, the filter delivery device can include a body 202. The body 202 of the filter delivery device 200 can be generally cylindrical and hollow. Also, the body 202 of the filter delivery device 200 can include a proximal end 204 and a distal end 206. A side port 208 can be formed in the body 202 of the filter delivery device 200 between the proximal end 204 of the body 202 and the distal end of the body 202. A saline drip infusion set 210 can be connected to the side port 208 of the body 202. In a particular embodiment, the saline drip infusion set 210 can be used to deliver saline to the patient during the delivery and deployment of an embolic filter using the filter delivery device 200.

As depicted in FIG. 2, an adapter 212 can be connected to the proximal end 204 of the body 202 of the filter delivery device 200. Also, a filter storage tube adapter 214 can be connected to the distal end 206 of the body of the filter delivery device 200. FIG. 2 shows that the filter delivery device 200 can also include a filter storage tube 216. The filter storage tube 216 can be hollow and generally cylindrical. Further, the filter storage tube 216 can include a proximal end 218 and a distal end 220. As shown, the proximal end 218 of the filter storage tube 216 can be coupled to the filter storage tube adapter 214. An introducer catheter 222 can be connected to the distal end 220 of the filter storage tube 216.

In a particular embodiment, an embolic filter 224 can be stored within the filter storage tube 216. As shown, the embolic filter 224 can be formed into a collapsed configuration and installed within the filter storage tube 216. The embolic filter 218 can be the embolic filter described below. Further, the embolic filter 218 can be made from a shape memory material. The shape memory material can be a shape memory polymer. Further, the shape memory material can be a shape memory metal. The shape memory metal can be a nickel titanium alloy such as nitinol.

FIG. 2 shows that a pusher wire 226 can be slidably disposed within the body 202 of the filter delivery device 200. The pusher wire 226 can be formed from an extremely flexible metal alloy, e.g., a nickel titanium alloy. The nickel titanium alloy can include nitinol. Further, the pusher wire 226 can extend through the body 202 of the filter delivery device 200 and into the filter storage tube 216. The pusher wire 226 can include a proximal end 228 and a distal end 230. A pusher wire handle 232 can be attached to, or otherwise formed with, the proximal end 228 of the pusher wire 226. The distal end 230 of the pusher wire 226 can extend into the filter storage tube 216 attached to the body 202. Further, the distal end 230 of the pusher wire 226 can include a pusher head 234 that can contact the embolic filter 218.

During installation of the embolic filter, the installation catheter 222 can be threaded into the cardiovascular system of a patient, e.g., the cardiovascular system 100 described above, in order to deliver and deploy the embolic filter to the desired location with the patient. For example, the installation catheter 222 can be threaded through the femoral artery into the inferior vena cava of the patient. A distal end of the installation catheter 222 can include a pair of radiopaque bands spaced a predetermined distance apart. Using fluoroscopy, the radiopaque bands can indicate when the distal end of the installation catheter 222 is located at or near the desired location within the inferior vena cava.

When the distal end of the installation catheter 222 is in the desired location within the inferior vena cava, the pusher wire 226 can be moved through the body 202 of the filter delivery device 200, through the filter storage tube 216 and into the installation catheter 222. As the pusher wire 226 is pushed through the filter storage tube 216, the embolic filter 224 is pushed from within the filter storage tube 216 into the installation catheter 222. The embolic filter 224 can be pushed through the installation catheter 222 until it is expelled from the distal end of the installation catheter 222 into the inferior vena cava. Upon exiting the installation catheter 222, the embolic filter 224 can be warmed by the body temperature of the patient. When the embolic filter 224 reaches approximately thirty-seven degrees Celsius (37° C.), e.g., normal body temperature, the embolic filter 224 can move from the collapsed configuration to an expanded configuration within the inferior vena cava. Thereafter, the installation catheter 222 can be withdrawn from the patient.

Description of an Embolic Filter

Figure 3:
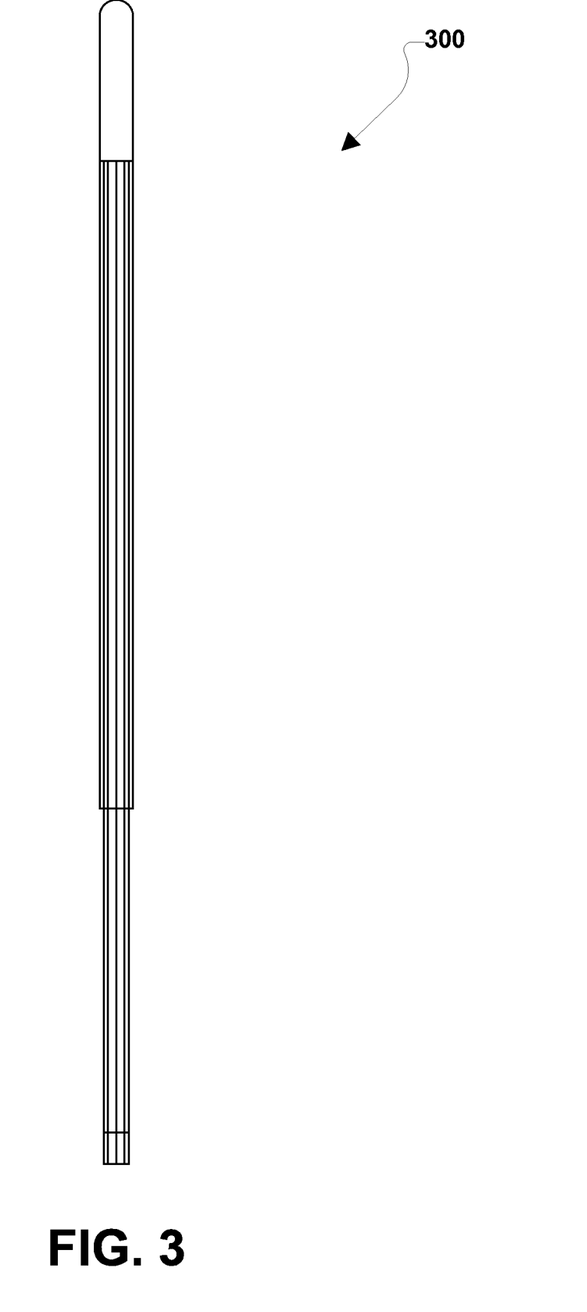
FIG. 3 is a plan view of an embolic filter in a collapsed configuration.
Figure 4:
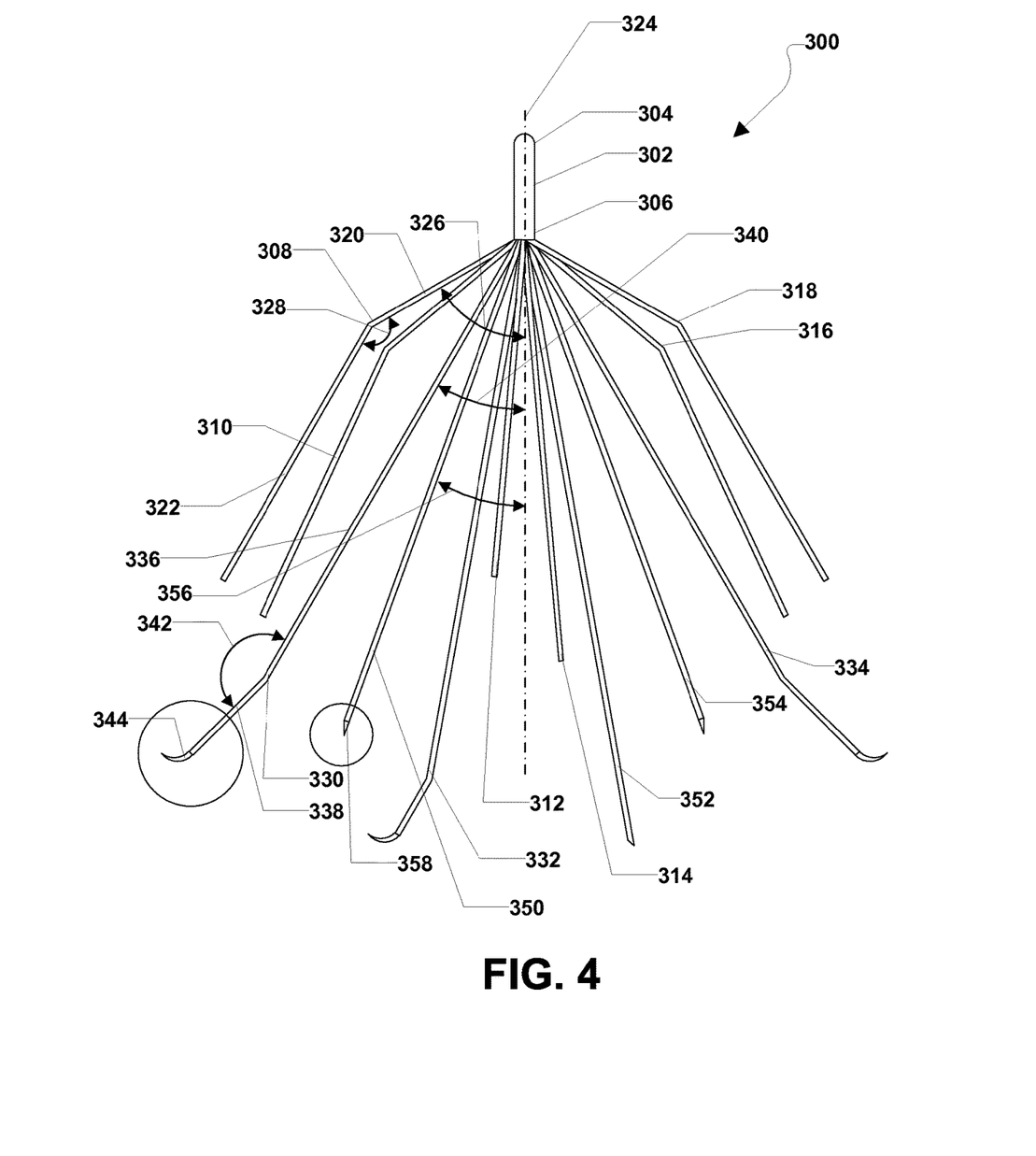
FIG. 4 is a plan view of the embolic filter in an expanded configuration.

Referring now to FIG. 3 and FIG. 4, an embolic filter is shown and is generally designated 300. As depicted in FIG. 4, the embolic filter 300 can include a head 302. The head 302 can be generally cylindrical and hollow. Further, the head 302 can have a proximal end 304 and a distal end 306. The proximal end 304 of the head 302 can be closed and the distal end 306 of the head 302 can be open. As such, the head 302 can be generally shaped like a test tube.

As indicated in FIG. 4, a first bent arm 308 can extend from the distal end 306 of the head 302. A second bent arm 310 can extend from the distal end 306 head 302. A third bent arm 312 can extend from the distal end 306 of the head 302. A fourth bent arm 314 can extend from the distal end 306 of the head 302. A fifth bent arm 316 can extend from the distal end 306 of the head 302. Further, a sixth bent arm 318 can extend from the distal end 306 of the head 302. Each bent arm 308, 310, 312, 314, 316, 318 can include a first portion 320 and a second portion 322. In the deployed, expanded configuration, shown in FIG. 4, the first portion 320 of each bent arm 308, 310, 312, 314, 316, 318 can extend from the head at an angle with respect to a longitudinal axis 324 to form a primary bent arm angle 326.

The primary bent arm angle 326 can be approximately forty-five degrees (45°). In another embodiment, the primary bent arm angle 326 can be approximately fifty degrees (50°). In yet another embodiment, the primary bent arm angle 326 can be approximately fifty-five degrees (55°). In still another embodiment, the primary bent arm angle 326 can be approximately sixty degrees (60°). In another embodiment, the primary bent arm angle 326 can be approximately sixty-five degrees (65°).

The second portion 322 can be angled with respect to the first portion 320 to form a secondary bent arm angle 328. In particular, the second portion 322 can be angled inward with respect to the first portion 320, e.g., toward the longitudinal axis 324 of the embolic filter 300.

In a particular embodiment, the secondary bent arm angle 328 can be approximately twenty degrees (20°). In another embodiment, the secondary bent arm angle 328 can be approximately twenty-five degrees (25°). In yet another embodiment, the secondary bent arm angle 328 can be approximately thirty degrees (30°). In still another embodiment, the secondary bent arm angle 328 can be approximately thirty-five degrees (35°). In another embodiment, the secondary bent arm angle 328 can be approximately forty degrees (40°). In yet still another embodiment, the secondary bent arm angle 328 can be approximately forty-five degrees (45°).

In a particular embodiment, each bent arm 308, 310, 312, 314, 316, 318 is movable between a straight configuration, shown in FIG. 3, and an angled configuration, shown in FIG. 4. When the embolic filter 300 is in the pre-deployed, collapsed configuration, shown in FIG. 3, the bent arms 308, 310, 312, 314, 316, 318 are substantially straight and substantially parallel to the longitudinal axis 324 of the embolic filter. When the embolic filter 300 moves to the deployed, expanded configuration, shown in FIG. 4, the bent arms 308, 310, 312, 314, 316, 318 can move to the angled and bent configuration shown in FIG. 4.

As further illustrated in FIG. 3, a first bent leg 330 can extend from the head 302. A second bent leg 332 can extend from the head 302. Moreover, a third bent leg 334 can extend from the head 302. Each bent leg 330, 332, 334 can include a substantially straight first portion 336 and a substantially straight second portion 338. The first portion 336 of each bent leg 330, 332, 334 can extend from the head 302 at an angle with respect to the longitudinal axis 324 to form a primary bent leg angle 340.

In a particular embodiment, the primary bent leg angle 340 can be approximately twenty degrees (20°). In another embodiment, the primary bent leg angle 340 can be approximately twenty-five degrees (25°). In yet another embodiment, the primary bent leg angle 340 can be approximately thirty degrees (30°). In still another embodiment, the primary bent leg angle 340 can be approximately thirty-five degrees (35°). In another embodiment, the primary bent leg angle 340 can be approximately forty degrees (40°). In yet still another embodiment, the primary bent leg angle 340 can be approximately forty-five degrees (45°).

The second portion 338 of each bent leg 330, 332, 334 can extend be angled with respect to the first portion 336 in order to form a secondary bent leg angle 342. Specifically, the second portion 338 can be angled outward relative to the first portion 336, e.g., away from the longitudinal axis 324 of the embolic filter 300.

In a particular embodiment, the secondary bent leg angle 342 is approximately five degrees (5°). In another embodiment, the secondary bent leg angle 342 is approximately ten degrees (10°). In still another embodiment, the secondary bent leg angle 342 is approximately fifteen degrees (15°). In yet another embodiment, the secondary bent leg angle 342 is approximately twenty degrees (20°). In another embodiment, the secondary bent leg angle 342 is approximately twenty-five degrees (25°).

In a particular embodiment, each bent leg 330, 332, 334 is movable between a straight configuration, shown in FIG. 3, and an angled and bent configuration, shown in FIG. 4. When the embolic filter 300 is in the pre-deployed, collapsed configuration, shown in FIG. 3, the bent legs 330, 332, 334 are substantially straight and substantially parallel to the longitudinal axis 324 of the embolic filter. When the embolic filter 300 moves to the deployed, expanded configuration, shown in FIG. 4, the bent legs 330, 332, 334 move to the angled and bent configuration shown in FIG. 4.

Figure 5:
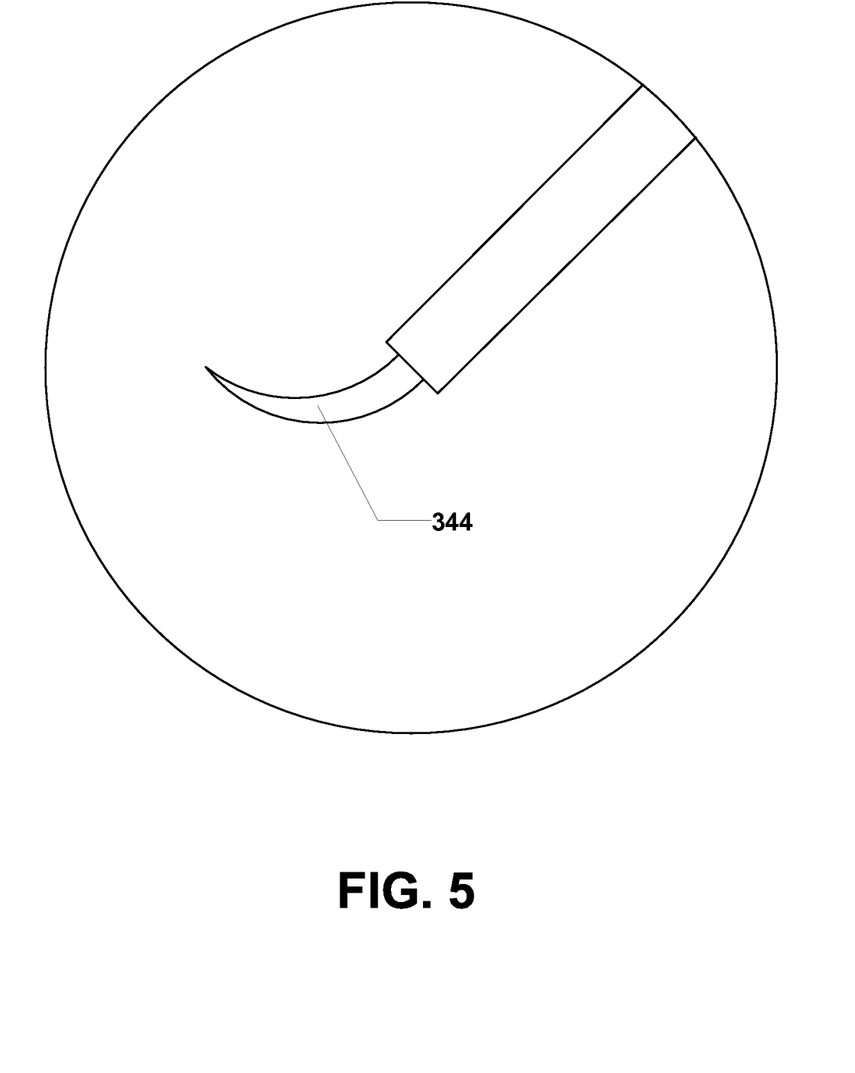
FIG. 5 is a detailed view of the embolic filter taken at circle 5 in FIG. 4.

Each bent leg 330, 332, 334 can also include a foot 344. As shown in FIG. 5, the foot 344 of each bent leg 330, 332, 334 can be curved to form a hook. Each hook can also form a barb. In particular each foot 344 can move from a straight configuration, shown in FIG. 3, to a curved configuration, shown in FIG. 4 and FIG. 5. As such, when the embolic filter 300 is in the collapsed configuration shown in FIG. 3, the feet 344 of the bent legs 330, 332, 334 are straight. When the embolic filter 300 moves to the expanded configuration, the feet 344 are bent. Further, when the feet 344 are bent, the feet 344 can extend into and engage the inner wall of a vein in which the embolic filter is installed. The feet 344 can substantially prevent cranial migration of the embolic filter 300. In other words, the feet 344 can engage the inner wall of the vein and substantially prevent the embolic filter 300 from moving upstream in a cranial direction within the vein due to blood flow through the embolic filter 300.

FIG. 4 indicates that the embolic filter 300 can include a first straight leg 350, a second straight leg 352, and a third straight leg 354. Each straight leg 350, 352, 354 can extend from the distal end 306 of the head 302. In the expanded configuration, in particular, each straight leg 350, 352, 354 can extend from the head 302 at an angle with respect to the longitudinal axis 324 to form a primary straight leg angle 356.

In a particular embodiment, the primary straight leg angle 356 can be approximately twenty degrees (20°). In another embodiment, the primary straight leg angle 356 can be approximately twenty-five degrees (25°). In yet another embodiment, the primary straight leg angle 356 can be approximately thirty degrees (30°). In still another embodiment, the primary straight leg angle 356 can be approximately thirty-five degrees (35°). In another embodiment, the primary straight leg angle 356 can be approximately forty degrees (40°). In yet still another embodiment, the primary straight leg angle 356 can be approximately forty-five degrees (45°).

Figure 6:
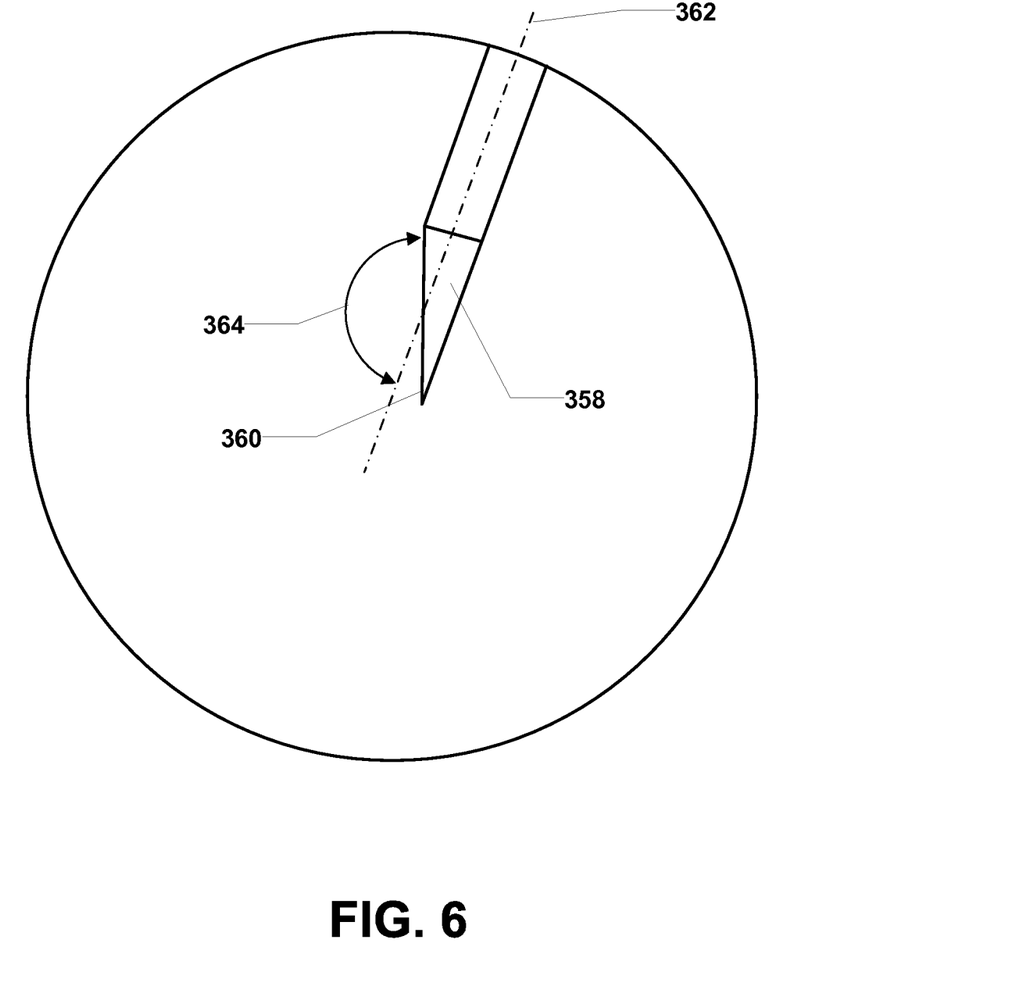
FIG. 6 is a detailed view of the embolic filter taken at circle 6 in FIG. 4.
Figure 8:
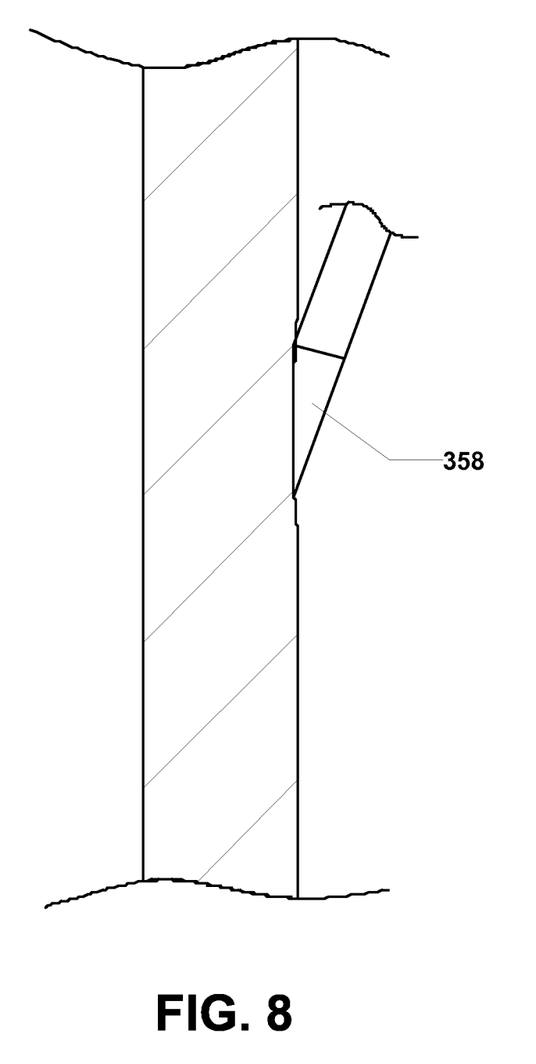
FIG. 8 is a plan view of the foot engaged with the inner wall of a vein.

Each straight leg 350, 352, 354 can include a distal end 358 that is configured to engage the inner wall of the vein in which the embolic filter 300 is installed. In particular, as shown in FIG. 6, the distal end 358 of each straight leg 350, 352, 354 can include a vein engagement face 360 that is configured to engage the inner wall of a vein, as shown in FIG. 8. Further, each vein engagement face 360 can be angled with respect to a longitudinal axis 362 defined by each straight leg 350, 352, 354 in order to establish a vein engagement face angle 364.

In a particular embodiment, the vein engagement face angle 364 can be ninety degrees (90°). In another embodiment, the vein engagement face angle 364 can be ninety-five degrees (95°). In still another embodiment, the vein engagement face angle 364 can be one hundred degrees (100°). In another embodiment, the vein engagement face angle 364 can be one hundred five degrees (105°). In yet another embodiment, the vein engagement face angle 364 can be one hundred ten degrees (110°). In another embodiment, the vein engagement face angle 364 can be one hundred fifteen degrees (115°).

In still yet another embodiment, the vein engagement face angle 364 can be one hundred twenty degrees (120°). In another embodiment, the vein engagement face angle 364 can be one hundred twenty five degrees (125°). In yet another embodiment, the vein engagement face angle 364 can be one hundred thirty degrees (130°). In another embodiment, the vein engagement face angle 364 can be one hundred thirty five degrees (135°). In another embodiment, the vein engagement face angle 364 can be one hundred forty degrees (140°). In another embodiment, the vein engagement face angle 364 can be one hundred forty five degrees (145°). In another embodiment, the vein engagement face angle 364 can be one hundred fifty degrees (150°).

Figure 7:
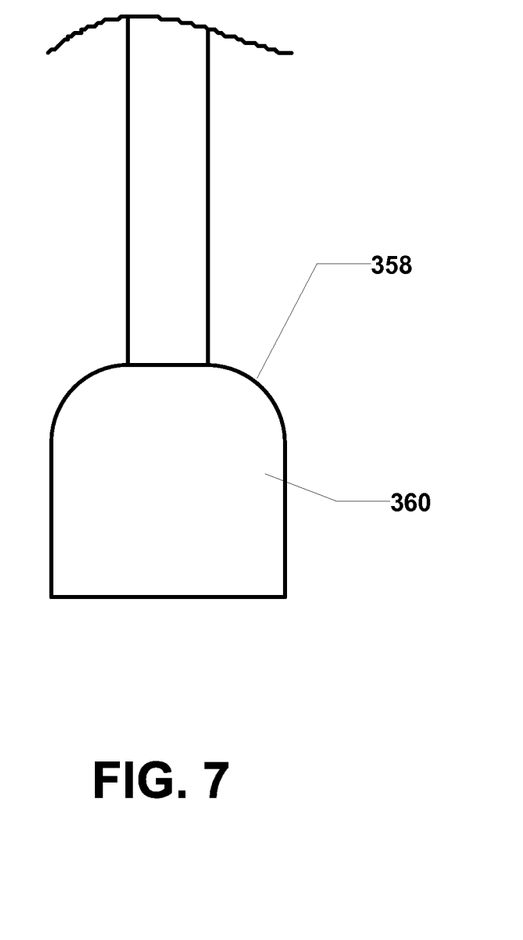
FIG. 7 is a plan view of a foot of the embolic filter.

As depicted in FIG. 7, the distal end 358 of each straight leg 350, 352, 354 can be enlarged. For example, the distal end 358 of each straight leg 350, 352, 354 can be generally spade-shaped. In a particular embodiment, a width of the distal end 358 is at least one and one-half times (1.5×) greater than a diameter of the straight leg 350, 352, 354. In another embodiment, the width of the distal end 358 is at least two times (2×) greater than the diameter of the straight leg 350, 352, 354. In yet another embodiment, the width of the distal end 358 is at least two and one-half times (2.5×) greater than the diameter of the straight leg 350, 352, 354. In still another embodiment, the width of the distal end 358 is at least three times (3×) greater than the diameter of the straight leg 350, 352, 354. The width of the distal end 358 of each straight leg 350, 352, 354 is not greater than the outer diameter of the head 302 of the embolic filter 300.

Enlarging the distal end 358 of each straight leg 350, 352, 354 can allow the vein engagement face 360 to be enlarged which can increase the engagement of the vein engagement face 360 with the vein in which the embolic filter 300 is installed. However, the distal end 358 of each straight leg 350, 352, 354 can have the same diameter as the straight leg 350, 352, 354.

In a particular embodiment, the vein engagement face 360 can be roughened. For example, the roughening process can include acid etching; application of a bead coating, e.g., cobalt chrome beads; application of a roughening spray, e.g., titanium plasma spray (TPS); laser blasting; or any other similar process or method. Roughening the vein engagement face 360 can increase the engagement of the vein engagement face 360 with the inner wall of the vein in which the embolic filter is installed. The vein engagement face 360 of each straight leg 350, 352, 354 can substantially prevent caudal migration of the embolic filter 300. In other words, the vein engagement face 360 can engage the inner wall of the vein and substantially prevent the embolic filter 300 from moving downstream in a caudal direction within the vein.

Each bent arm 308, 310, 312, 314, 316, 318 can include a bent arm length. Further, each bent leg 330, 332, 334 can include a bent leg length. Moreover, each straight leg 350, 352, 354 can include a straight leg length. In a particular embodiment, the bent arm length is approximately six-tenths times (0.6×) the bent leg length. In another embodiment, the bent arm length is approximately six and one-half tenths times (0.65×) the bent leg length. In yet another embodiment, the bent arm length is approximately seven-tenths times (0.7×) the bent leg length. In still another embodiment, the bent arm length is approximately seven and one-half tenths times (0.75×) the bent leg length. In another embodiment, the bent arm length is approximately eight tenths times (0.8×) the bent leg length.

In a particular embodiment, the straight leg length is approximately ninety-five one hundreds times (0.95×) the bent leg length. In another embodiment, the straight leg length is approximately ninety-six one hundreds times (0.96×) the bent leg length. In yet another embodiment, the straight leg length is approximately ninety-seven one hundreds times (0.97×) the bent leg length. In still another embodiment, the straight leg length is approximately ninety-eight one hundreds times (0.98×) the bent leg length. In another embodiment, the straight leg length is approximately ninety-nine one hundreds times (0.99×) the bent leg length. In yet another embodiment, the straight leg length is approximately equal to the bent leg length.

During installation and deployment, the vein engagement face 360 of each straight leg 350, 352, 354 can allow the embolic filter 300 to move in a cranial direction. As such, the embolic filter 300 can be moved in the cranial direction to allow the bent legs 330, 332, 334, e.g., the feet 344 thereof, to engage the inner wall of the vein. The straight legs 350, 352, 354, however, can prevent the embolic filter 300 from moving caudally and allowing the feet 344 of the bent legs 330, 332, 334 to disengage from the inner wall of the vein. As such, the embolic filter 300 can be substantially locked and place within the vein and the embolic filter 300 can be prevented from moving cranially or caudally within the vein. In a particular embodiment, cranial migration is toward a patient's head and caudal migration is longitudinally opposite the cranial migration, i.e., toward a patient's lower end.

Figure 9:
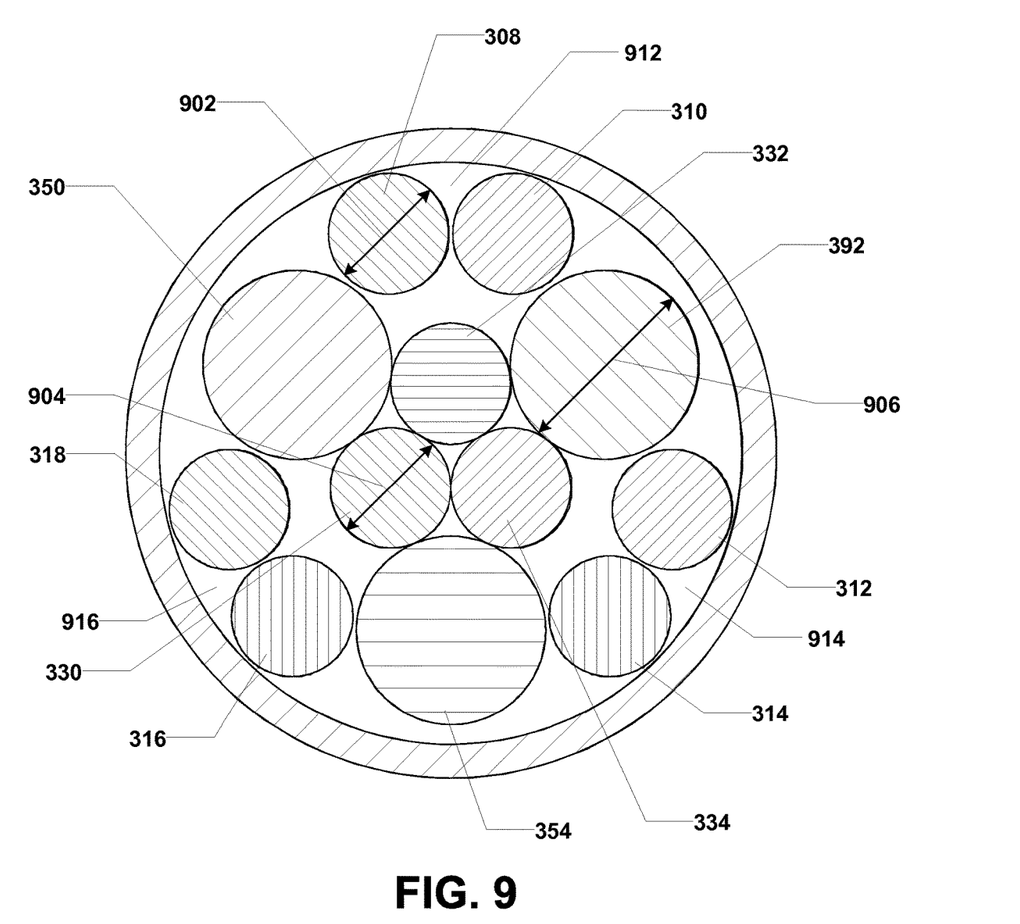
FIG. 9 is a cross-section view of the embolic filter taken at line 8-8 in FIG. 4.

Referring now to FIG. 9, a cross-section view of the head 302 of the embolic filter 300 is shown. As shown, each bent arm 308, 310, 312, 314, 316, 318 can have a bent arm diameter 902. In a particular embodiment, the bent arm diameter 902 can be in a range of ten thousands of an inch to fifteen thousands of an inch (0.010"-0.015"). Each bent leg 330, 332, 334 can have a bent leg diameter 904. The bent leg diameter 904 can be in a range of ten thousands of an inch to fifteen thousands of an inch (0.010"-0.015"). Each straight leg 350, 352, 354 can have a straight leg diameter 906. The straight leg diameter 906 can be in a range of eighteen thousands of an inch to thirty thousands of an inch (0.018"-0.030"). As such, each straight leg 350, 352, 354 can have a stiffness that is greater than a stiffness of each bent leg 330, 332, 334 and a stiffness of each bent arm 308, 310, 312, 314, 316, 318.

A ratio of the bent arm diameter 902 to the straight leg diameter 906 is in a range of 0.33 to 0.83. Also, a ratio of the bent leg diameter 904 to the straight leg diameter 906 is in a range of 0.33 to 0.83. Stated differently, the straight leg diameter 906 is at least one and two-tenths times (1.2×) greater than the bent leg diameter 904, or the bent arm diameter 902. Further, in the straight leg diameter 906 is not greater than three times (3×) greater than the bent leg diameter 904, or the bent arm diameter 902. The relatively larger diameter can provide additional stiffness that is desirable to prevent caudal migration. For example, the increased stiffness of the straight legs 350, 352, 354 can cause the straight legs 350, 352, 354 to splay radially outward and provide an outward force to maintain the vein engagement face 360 of each straight leg 350, 352, 354 in contact with the inner wall of the vein in which the embolic filter 300 is installed. Accordingly, the stiffer legs can decrease the likelihood of caudal migration of the embolic filter 300.

The cross-section view shows a first arrangement of the arms 308, 310, 312, 314, 316, 318 and legs 330, 332, 334, 350, 352, 354 within the head 302 of the embolic filter 300. In order to minimize the invasion of the patient during the installation of the embolic filter 300, it may be desirable to minimize the outer diameter of the head 302 of the embolic filter 300. Minimizing the outer diameter can result in a minimized internal diameter of the embolic filter 300. In order to fit within the head 302, the arms 308, 310, 312, 314, 316, 318 and legs 330, 332, 334, 350, 352, 354 can be arranged as shown in FIG. 9. In a particular embodiment, when collapsed, the embolic filter can be installed using a seven French catheter. In another embodiment, the embolic filter can be installed using a six French catheter. In still another embodiment, the embolic filter can be installed using a five French catheter.

For example, the bent legs 330, 332, 334, e.g., the proximal ends thereof, can be arranged around the center of the head, e.g., the point through which the longitudinal axis (not shown in FIG. 9) of the embolic filter 300 passes, so that the centers of the bent legs 330, 332, 334 form an equilateral triangle. Further, the proximal end of the first straight leg 350 can be placed in contact with the proximal end of the first bent leg 330 and the proximal end of the second bent leg 332. The proximal end of the second straight leg 352 can be placed in contact with the proximal end of the second bent leg 332 and the proximal end of the third bent leg 334. Also, the proximal end of the third straight leg 354 can be placed in contact with the proximal end of the third bent leg 334 and the proximal end of the first bent leg 330. Accordingly, the centers of the straight legs 350, 352, 354 can also form an equilateral triangle.

Thereafter, the proximal ends of the first and second bent arms 308, 310 can be placed adjacent to each other within a first space 912 bound by the first straight leg 350, the second bent leg 332 and the second straight leg 352. The proximal ends of the third and fourth bent arms 312, 314 can be placed adjacent to each other within a second space 914 bound by the second straight leg 352, the third bent leg 334 and the third straight leg 354. Moreover, the proximal ends of the fifth and sixth bent arms 316, 318 can be placed adjacent to each other within a third space 916 bound by the third straight leg 354, the first bent leg 330 and the first straight leg 334.

Figure 10:
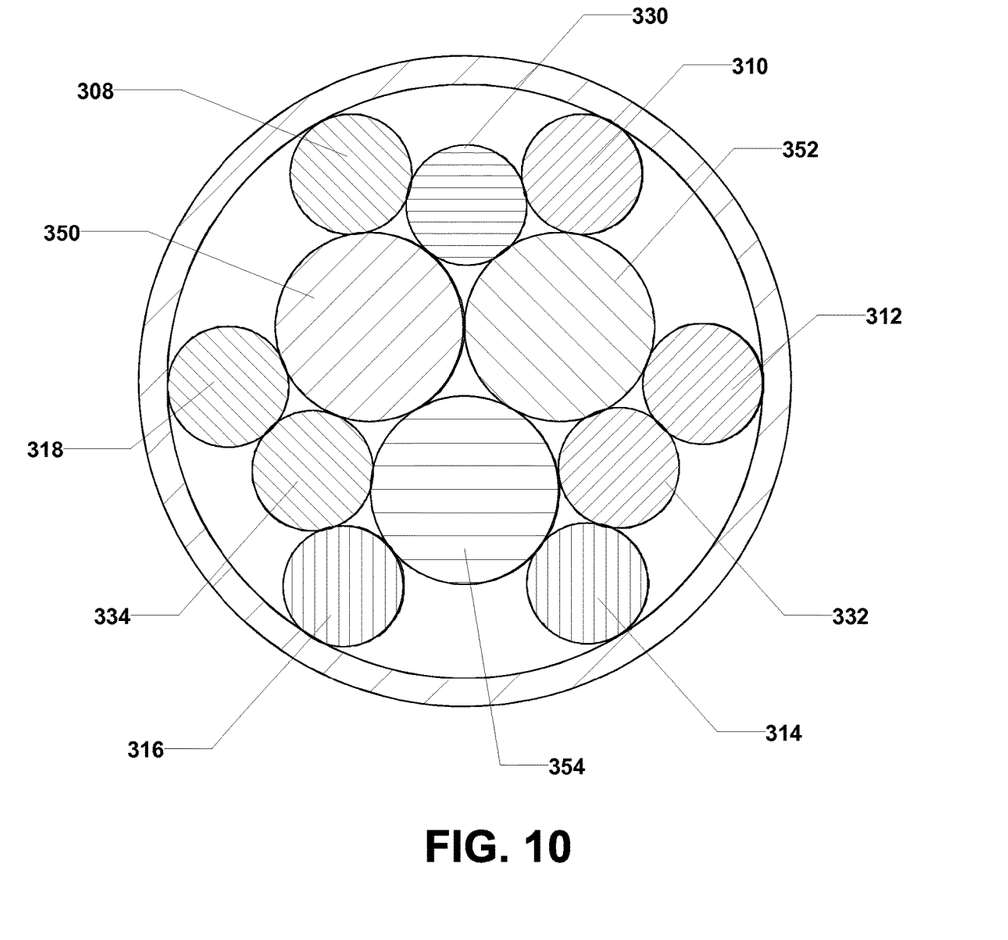
FIG. 10 is an alternative cross-section view of the embolic filter.

Referring to FIG. 10, an alternative arrangement of the arms 308, 310, 312, 314, 316, 318 and legs 330, 332, 334, 350, 352, 354 within the head 302 is shown. FIG. 10 shows that the proximal ends of the straight legs 350, 352, 354 can be arranged around the center of the head, e.g., the point through which the longitudinal axis (not shown in FIG. 10) of the embolic filter 300 passes, so that the centers of the straight legs 350, 352, 354 form an equilateral triangle.

The proximal end of the first bent leg 330 can be placed in contact with the proximal end of the first straight leg 350 and the proximal end of the second straight leg 352. The proximal end of the second bent leg 332 can be placed in contact with the proximal end of the second straight leg 352 and the proximal end of the third straight leg 354. Further, the proximal end of the third bent leg 334 can be placed in contact with the proximal end of the third straight leg 354 and the proximal end of the first straight leg 350. As such, the centers of the bent legs 330, 332, 334 also form an equilateral triangle. Further, the proximal end of the first straight leg 350 can be placed in contact with the proximal end of the first bent leg 330 and the proximal end of the second bent leg 332. The proximal end of the second straight leg 352 can be placed in contact with the proximal end of the second bent leg 332 and the proximal end of the third bent leg 334. Also, the proximal end of the third straight leg 354 can be placed in contact with the proximal end of the third bent leg 334 and the proximal end of the first bent leg 330.

Thereafter, the proximal ends of the first and second bent arms 308, 310 can be placed on each side of the proximal end of the first bent leg 330 so that the proximal ends of the first and second bent arms 308, 310 flank the proximal end of the first bent leg 330. The proximal ends of the third and fourth bent arms 312, 314 can be placed on each side of the proximal end of the second bent leg 332 so that the proximal ends of the third and fourth bent arms 312, 314 flank the proximal end of the second bent leg 332. Moreover, the proximal ends of the fifth and sixth bent arms 316, 318 can be placed on each side of the proximal end of the third bent leg 334 so that the proximal ends of the fifth and sixth bent arms 316, 318 flank the proximal end of the third bent leg 334.

CONCLUSION

With the configuration of structure described above, one or more of the embodiments described herein can provide a device that can be permanently or temporarily installed within a patient, e.g., within an inferior vena cava of a patient. The embodiments described herein can include a plurality of bent arms that provide lateral stability and maintain the embolic filter substantially centered within the inferior vena cava. Further, features of the embodiments described herein can include a plurality of bent legs that extend in generally the same direction as the bent arms. Each bent leg can include a foot that can be formed with a hook or a barb. The feet of the bent legs can engage the inner wall of the inferior vena cava and can substantially prevent cranial migration of the embolic filter.

Moreover, the embodiments described herein can include a plurality of straight legs. Each straight leg can include a vein engagement face that can engage the inferior vena cava in a direction opposite the feet of the bent legs. The vein engagement faces can prevent caudal migration of the embolic filter. Accordingly, when the embolic filter is placed within the inferior vena cava it can remain substantially within the original location in which it is placed until it is removed.

The embolic filter, as described herein, includes six arms and six legs. It can be appreciated that the embolic filter can include more or less than six arms and more or less than six legs. Further, the embolic filter, as described herein, includes three bent legs and three straight legs. However, the embolic filter can include other combinations of bent legs and straight legs, e.g., four bent legs and two straight legs, two bent legs and four straight legs, etc. Also, the straight legs can be formed similar to the bent legs, e.g., with a bend, while retaining the relatively larger diameter. Additionally, one or more of the arms can be formed similar to the straight legs, e.g., with or without a bend, with an enlarged distal end, with a vein engagement face, or a combination thereof.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An embolic filter, comprising:
  a) a head having a proximal end, a distal end having a first position, and a filter central longitudinal axis;
  b) a plurality of appendages that include straight leg appendages and bent leg appendages, each of said plurality of appendages extending distally from the first position on the distal end of the head, said plurality of appendages including a first plurality of appendages providing a distal appendage end with a curved anchor, said curved anchor configured to engage an inner wall of a vein at a location spaced distally of the head and prevent the embolic filter from migrating in a cranial direction;
  c) the said plurality of appendages including a second plurality of appendages that are said straight leg appendages, each having a straight leg central longitudinal axis, each straight leg appendage extending distally from the head at said first position, wherein each appendage of the second plurality has a distal most end, said distal most end having a caudal anchor located distally of the head and joined to the straight leg appendage, each said caudal anchor having a vein engagement surface configured to engage an inner wall of a vein at a location spaced distally of the head to prevent the embolic filter from migrating in a caudal direction;

d) wherein said straight leg central longitudinal axis intersects said vein engagement surface;

e) wherein the curved anchor is of a different configuration as compared to the caudal anchor of the straight legs;

f) wherein each said caudal anchor has a distal most tip, said vein engagement surface located proximally of said distal most tip and wherein there is a taper between the distal most tip and the said straight leg appendage proximally of said distal most tip, wherein said vein engagement surface is located at said taper and forms an obtuse angle with said straight leg appendage central axis;

g) wherein one or more of the appendages of the first plurality are longer than one or more of the appendages of the second plurality;

h) the filter having a pre-deployment position that aligns all of the appendages together distally of the head and next to said filter central longitudinal axis;

i) the filter having a deployed position wherein all of the appendages are spaced radially away from said filter central longitudinal axis, and wherein said vein engagement surface is configured to abut the vein inner wall; and j) wherein in both the pre-deployment and deployed positions the said curved anchors and caudal anchors are closer to each other and closer to said filter central longitudinal axis than to the head.

2. The embolic filter of claim 1, wherein the caudal anchor is tapered to provide a smaller end portion spaced away from the head and a larger portion in between the smaller portion and the head.

3. The embolic filter of claim 2, wherein the straight leg appendages form an acute angle with the filter central longitudinal axis in the deployed position.

4. The embolic filter of claim 2, wherein said vein engagement surface being generally aligned with the central longitudinal axis of the head.

5. The embolic filter of claim 1, wherein each caudal anchor vein engagement surface faces away from said filter central longitudinal axis and that is angled to define an obtuse angle relative to a said straight leg appendage of the second plurality.

6. The embolic filter of claim 1 wherein there is a bent appendage angle of between about 45 and 65 degrees between each bent appendage and said longitudinal axis.

7. The embolic filter of claim 1 wherein each bent appendage forms an angle of between about 20 degrees and 45 degrees with said longitudinal axis.

8. The embolic filter of claim 1 wherein each of the first plurality of appendages has a secondary bend angle of between about 5 and 25 degrees.

9. The embolic filter of claim 1 wherein each of the second plurality of appendages forms an angle of between about 20 and 45 degrees with said longitudinal axis.

10. Apparatus including the embolic filter of claim 1 and a filter delivery system that includes a catheter and wherein when the embolic filter is in a collapsed position within the catheter, the plurality of appendages extend in one direction from the head.

11. The embolic filter of claim 1 wherein a bend divides each of the first plurality of appendages into proximal and distal sections, the proximal section forming a first acute angle with the head axis, the distal section forming a second acute angle with the head axis that is larger than the first angle.

12. An embolic filter, comprising:

a) a head having a proximal end, a distal end having a first position, and a head central longitudinal axis;

b) a first plurality of legs extending from the first position of the distal end of the head, wherein each of the first plurality of legs has a distal end with a curved distal anchor that is the most distal part of each leg of the first plurality and that is located distally of the head, said curved distal anchor configured to curve away from said head central longitudinal axis, said curved anchor having a hook end that is positioned to engage an inner wall of a vein at a location spaced distally of the head and prevent the embolic filter from migrating in a cranial direction and wherein each of the first plurality of legs has a first leg diameter;

c) a second plurality of legs extending from the first position of the distal end of the head, wherein each of the second plurality of legs is a straight leg having a straight leg central longitudinal axis and a distal end with a caudal anchor that is configured to engage an inner wall of a vessel, said caudal anchor includes a distal pointed tip that is the most distal part of said straight leg and an angled vessel engaging surface proximal to said distal pointed tip and wherein each of the second plurality of legs has a second leg diameter;

d) wherein the first and second plurality of legs have a deployed position wherein each of the legs forms an acute angle with the head central longitudinal axis;

e) wherein said angled vessel engaging surface is positioned to engage the inner wall of a vessel at a position spaced distally of the head, said angled vessel engaging surface positioned away from said head longitudinal axis and configured to prevent the embolic filter from migrating in a caudal direction;

f) wherein the angled vessel engaging surface forms an angle with the straight leg that is not a right angle;

g) wherein said caudal anchor is tapered, gradually thickening proximally of said distal pointed tip;

h) wherein said straight leg central longitudinal axis intersects said angled vessel engaging surface;

i) wherein said angled vessel engaging surface is configured to abut the vessel wall in the deployed position;

j) wherein each of said legs of the second plurality is shorter than each of the legs of the first plurality;

k) the filter having a pre-deployment position that aligns all of the legs together distally of the head and next to said central longitudinal axis;

l) wherein in both the pre-deployment and deployed positions each said curved anchor is closer to a said caudal anchor and to said head central longitudinal axis than to the head; and m) wherein the curved anchor is of a different configuration as compared to the caudal anchor of the straight legs.

13. The embolic filter of claim 12, wherein the first leg diameter of one leg in the first plurality of legs is at most 3 times greater than the second leg diameter of one leg in the second plurality of legs.

14. The embolic filter of claim 13, wherein the distal end angled vessel engaging surface of the caudal anchor is configured to engage an inner wall of a vein with a surface that forms an angle with the straight leg and wherein the surface is generally aligned with the inner wall of the vein when the filter is deployed in the vein in said deployed position, said surface preventing the embolic filter from moving in a caudal direction within the vein.

15. The embolic filter of claim 14, wherein the distal end of each of the second plurality of legs has a diameter that is at least one and one-half times (1.5×) greater than the second leg diameter, wherein there are more of said legs of the second plurality with the second leg diameter and in said pre-deployment position at least some of the legs of the second plurality are spaced radially outwardly of the legs of the first plurality.

16. The embolic filter of claim 14, wherein in the deployed position the vessel engaging surface is configured to align with and engage an inner wall of a vein and prevent the embolic filter from moving in a caudal direction within the vein.

17. The embolic filter of claim 16, wherein each vessel engaging surface is roughened.

18. Apparatus including the embolic filter of claim 12 and a filter delivery system that includes a catheter and wherein when the embolic filter is in a collapsed position within the catheter, the straight leg appendages and bent leg appendages extend in one direction from the head.

19. The embolic filter of claim 12, wherein the distal end of each of the second plurality of legs is tapered to provide a surface that is configured to engage an inner wall of a vein and prevent the embolic filter from migrating in a caudal direction, said surface being generally aligned with the central longitudinal axis of the head.

20. An embolic filter having a filter central longitudinal axis and configured for placement in a patient's vessel having a vessel wall, comprising:
   a) a head having a proximal end, a distal end and a head length;
   b) a plurality of bent appendages that extend distally from the head distal end, each having a bend that is spaced distally away from the head a distance greater than said head length;
   c) a second plurality of appendages that are straight leg appendages, each straight leg appendage having a straight appendage central longitudinal axis;
   d) a third plurality of appendages that are each shorter than any appendage of the first or second plurality of appendages;
   e) the plurality of bent appendages having curved anchor ends spaced distally away from the head that define first anchors, the first anchors configured to engage the vessel wall of a vein distally of the head to prevent movement of the filter in a first direction within a blood vessel;
   f) the plurality of the straight leg appendages having ends that are spaced distally away from the head that define second anchors, the second anchors configured to prevent movement of the filter in a second direction that is opposite said first direction;
   g) each of said second anchors having a distal most tip and a taper that extends proximally of said distal most tip, each of said second anchors including a vessel engaging surface that faces away from said filter central longitudinal axis and that faces toward said vessel wall, said vessel engaging surface forming an obtuse angle with said straight leg appendage central axis;
   h) wherein said straight leg central longitudinal axis intersects said vessel engaging surface;
   i) wherein the said first anchors are of a configuration that differs from the configuration of the said second anchors;
   j) the filter having a pre-deployment position that aligns all of the appendages together distally of the head and next to said central longitudinal axis;
   k) the filter having a deployed position wherein all of the appendages are spaced radially away from said filter central longitudinal axis;
   l) wherein the spacing between the said first anchor or the said second anchor in both pre-deployment and deployed positions is smaller than the spacing between the head and a said first anchors and said second anchors; and
   m) wherein in said pre-deployed position, said first anchor and said second anchor are closer to said filter central longitudinal axis, then to said head.

21. The embolic filter of claim 20, wherein each bent appendage includes a center and wherein the proximal ends of the bent appendages are arranged within the head so that the centers of the bent appendages form an equilateral triangle within the head.

22. The embolic filter of claim 21, wherein the proximal ends of the straight appendages are each disposed within the head in contact with the proximal ends of the bent appendages.

23. The embolic filter of claim 21 wherein the head has a generally cylindrically shaped wall, and wherein some of the appendages are in contact with the wall and with one or more other appendages.

24. The embolic filter of claim 22 wherein the head has a generally cylindrically shaped wall, and wherein some of the straight appendages are in contact with the wall and with one or more bent appendages.

25. Apparatus including the embolic filter of claim 20 and a filter delivery system that includes a catheter and wherein when the embolic filter is in a collapsed position within the catheter, the plurality of appendages extend in one direction from the head.

26. The embolic filter of claim 20 wherein the head has a central longitudinal axis, each bent appendage has a distal end and a bend in between the head and the distal end that divides each bent appendage into proximal and distal sections, the proximal section of each bent appendage forming a first acute angle with the head axis, the distal section of each bent appendage forming a second acute angle with the head axis that is larger than the first angle.

* * * * *

UNITED STATES PATENT AND TRADEMARK OFFICE
CERTIFICATE OF CORRECTION

PATENT NO. : 10,390,925 B2
APPLICATION NO. : 14/317442
DATED : August 27, 2019
INVENTOR(S) : Jenna Weidman It is certified that error appears in the above-identified patent and that said Letters Patent is hereby corrected as shown below:

In the Claims

Column 14, Line 39, claim "22" should be claim "21".

Signed and Sealed this
First Day of October, 2019

Andrei Iancu
*Director of the United States Patent and Trademark Office*